United States Patent
Vermeire et al.

(10) Patent No.: US 7,332,902 B1
(45) Date of Patent: Feb. 19, 2008

(54) MICRO SENSOR FOR ELECTROCHEMICALLY MONITORING RESIDUE IN MICRO CHANNELS

(75) Inventors: Bert M. Vermeire, Phoenix, AZ (US); Farhang F. Shadman, Tucson, AZ (US)

(73) Assignee: Environmental Metrology Corporation, Tucson, AZ (US)

( * ) Notice: Subject to any disclaimer, the term of this patent is extended or adjusted under 35 U.S.C. 154(b) by 18 days.

(21) Appl. No.: 11/205,582

(22) Filed: Aug. 16, 2005

Related U.S. Application Data

(60) Provisional application No. 60/624,131, filed on Nov. 2, 2004.

(51) Int. Cl.
  *G01N 27/00* (2006.01)
  *G01N 27/26* (2006.01)
  *G01R 27/28* (2006.01)

(52) U.S. Cl. ............... 324/71.4; 324/627; 204/451; 204/452

(58) Field of Classification Search .......... 324/71.4, 324/627; 204/451, 452
See application file for complete search history.

(56) References Cited

U.S. PATENT DOCUMENTS

| | | | | |
|---|---|---|---|---|
| 6,145,384 A | * | 11/2000 | Ikeda et al. | 73/780 |
| 6,294,063 B1 | * | 9/2001 | Becker et al. | 204/450 |
| 6,437,551 B1 | * | 8/2002 | Krulevitch et al. | 324/71.1 |
| 6,903,918 B1 | * | 6/2005 | Brennan | 361/306.1 |
| 2003/0156998 A1 | * | 8/2003 | Gilligan et al. | 422/102 |

OTHER PUBLICATIONS

K. Romero et al "In-situ analysis of wafer surface and deep trench rinse," Cleaning Technology in Semiconductor Device Manufacturing VI, The Electrochemical Society, 2000.

A.D. Hebda et al, "Fundamentals of UPW rinse: analysis of chemical removal from flat and patterned wafer surfaces" Cleaning Technology in Semiconductor Device Manufacturing VI, The Electrochemical Society, 2000.

J. Yan et al. "Test Structures for Analyzing Mechanisms of Wafer Chemical Contaminant Removal", IEEE International Conference on Microelectronic Test Structures, pp. 209-213, Mar. 2003.

* cited by examiner

*Primary Examiner*—Andrew H. Hirshfeld
*Assistant Examiner*—Amy He
(74) *Attorney, Agent, or Firm*—Eric A. Gifford

(57) ABSTRACT

The present invention provides a micro sensor for monitoring the cleaning and drying processes for very high aspect ratio micro channels in dielectric films oriented parallel to the fluid-solid interface during the manufacture of ICs, MEMS and other micro-devices. The micro sensor can be used to monitor "vertical" micro features common in microelectronics fabrication or "horizontal" micro features found in MEMS or microfluidic fabrication. By forming the micro channels parallel to the interface, the channels can be made with much higher and well controlled aspect ratios. In addition, multiple sensors can sense the impedance at various points along the micro features. The addition of a guard reduces the effects of any parasitic capacitance, which extends the measurement bandwidth of the sensor.

23 Claims, 13 Drawing Sheets

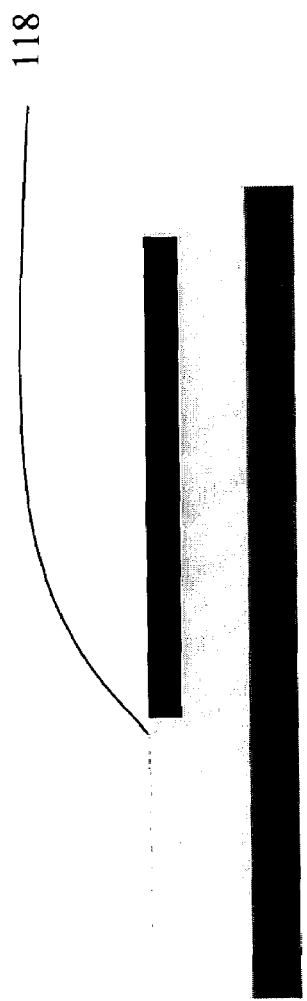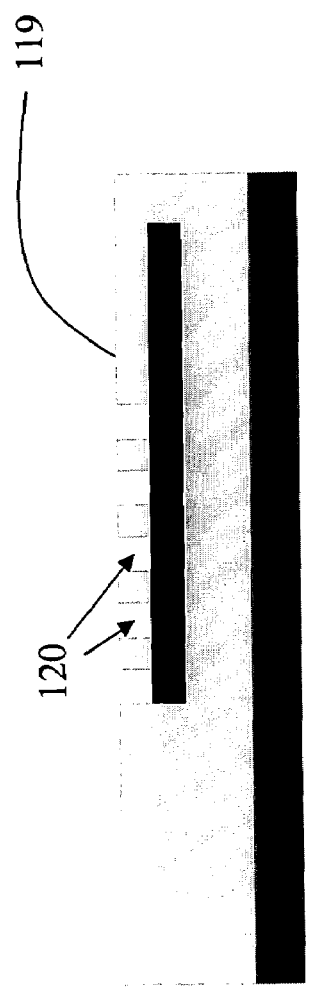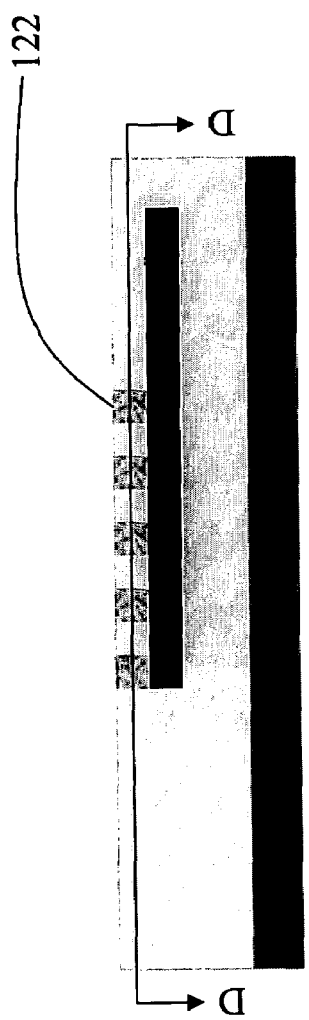

MICRO SENSOR FOR ELECTROCHEMICALLY MONITORING RESIDUE IN MICRO CHANNELS

CROSS-REFERENCE TO RELATED APPLICATIONS

This application claims benefit of priority under 35 U.S.C. 119(e) to U.S. Provisional Application No. 60/624,131 entitled "Method For Impedance Monitoring Of Fluids And Gases In High Aspect Ratio Structures And Method For Manufacturing Such A Monitor" filed on Nov. 2, 2004, the entire contents of which are incorporated by reference.

BACKGROUND OF THE INVENTION

1. Field of the Invention

This invention relates to monitoring the cleaning and drying processes during the manufacture of ICs, MEMS and other micro devices and more specifically to a micro sensor for high aspect ratio micro channels in dielectric films oriented parallel to the fluid-solid interface to emulate either "vertical" or "horizontal" micro features.

2. Description of the Related Art

A major challenge in manufacturing of the micro and nano devices is the cleaning and drying of very small void features ("micro features"), particularly those with large aspect ratios. These micro features are fabricated in various processing steps and can be very small voids such as gaps, holes, vias or trenches that are intentionally etched. The micro features can also be pores (voids) in a deposited dielectric material. Cleaning and drying occur repeatedly during the processing chain and are responsible for a significant part of the total processing time and for the consumption of much of the water, chemicals and energy.

In semiconductor manufacturing, trenches and vias are fabricated both in the device level and in the interconnect level. Most of these features have high aspect ratios with submicron openings and are therefore very difficult to clean and dry. In Integrated Circuits, MEMS and other micro device manufacturing, well controlled cleaning and drying are essential to avoid deformation of layers and improper adhesion of moving parts. Improper cleaning and drying would have a significant effect on manufacturing yield and device performance and reliability in both semiconductor and MEMS fabrication. Over-cleaning, over-rinsing or over-drying results in excessive use of chemicals, water and energy and also increases cycle time and potentially causes yield loss. Therefore, there is a strong economic and environmental incentive to use a process that is "just good enough".

The fine structures left behind after processes such as etching, deposition, and patterning, need to be cleaned and the reaction by-products need to be removed often down to trace levels. This usually involves three steps: 1) application of a cleaning solution; 2) rinsing and/or purging using ultra pure water or other rinsing solutions; and 3) drying by removing and purging the traces of any solvents used during rinsing. Due to the undesirable surface tension associated with aqueous chemicals and non-wetting nature of most future dielectrics, industry is pursing the development of processes based on supercritical fluids such as supercritical carbon dioxide for cleaning and pattern development. Measurement of cleanliness under these processing conditions is very critical.

Cleaning, rinsing, and subsequent drying processes are often performed and controlled almost "blindly" and based on trial and error or past experience. The way these processes are monitored and controlled presently is based on ex-situ testing of wafer, chips, or structures. Within the process tool, fixed recipes are provided by tools and process suppliers. Run-by-run adjustments or control are based on external and delayed information on product performance or product yields. The key reason for this inefficient and costly approach is that no sensors or techniques are available to measure the cleanliness and monitor the removal of impurities from micro features—to measure cleanliness where it actually counts. The sensors that are currently available are used in the fabs to monitor the conditions of fluid inside the process vessels and tanks, but far away from the inside of micro features (that is what needs to be monitored; it is also the bottleneck of cleaning and drying). The present monitoring techniques and devices do not provide realistic and accurate information on the cleanliness and condition of micro features.

Industry currently works around this problem while waiting for a solution; the process condition and cleaning and drying are often set with very large factors of safety (over-cleaning and over-rinsing). Large quantities of water and other chemicals are used (much more than what is really needed). This results in wasted chemicals, increased process time, lowered throughput, increased cost, and it causes reliability issues because of lack of process control.

K. Romero et al "In-situ analysis of wafer surface and deep trench rinse," Cleaning Technology in Semiconductor Device Manufacturing VI, The Electrochemical Society, 2000 propose a trench device for monitoring the process in-situ. As shown in FIG. 1, a trench device 10 comprises a pair of conducting electrodes (Poly-Si) 12 and 13 sandwiched between dielectric ($SiO_2$) layers 16 and 17 on opposite sides of a trench 14 on a substrate 18. Trench 14 is oriented perpendicular to the fluid-solid interface 19 of the device. An impedance analyzer 20 applies a measurement voltage 21 to the electrodes, which carry the measurement signal (voltage and current) to the trench. The impedance analyzer measures the impedance between its two terminals (ratio of voltage and current and the phase difference between the voltage and current).

Standard fabrication techniques limit the ability to form very deep trenches that are also very narrow, hence the aspect ratio of the trench. Furthermore, these deep etch techniques are not particularly well controlled so the actual aspect ratio of a particular trench may deviate significantly from the aspect ratio of the micro feature it is intended to emulate. In addition, the trench device can only emulate "vertical" micro features, which are common in microelectronics processing. However, MEMS and microfluidic devices often include "horizontal" micro features. Thus the trench device limits the type and aspect ratio of micro features that can be monitored and the accuracy of the monitoring. The trench device includes a single sensor (pair of electrodes) that measures the impedance at a single depth in the trench. Multiple electrodes at different depths in the trench device would require extra manufacturing steps and therefore substantially increase its cost.

Furthermore, for the sensor to be useful as a monitor of the fluid in the micro feature, the total parasitic capacitance between the electrodes and the substrate and/or fluid must be sufficiently small to allow an electrical measurement of the total impedance between the electrodes to resolve the solution resistance $R_{sol'n}$ and/or the interface double layer capacitance $C_{dl}$. If the parasitic capacitance dominates the total electrical response, then the circuit will not have a good signal to noise ratio and the sensor will not be very sensitive.

In the paper by Romero et al., the parasitic capacitance was found to dominate the solution resistance. At the parasitic capacitance measured (88 pF), the equivalent circuit calculation predicts no discernable impedance variation between highest and lowest trench resistances. The full ionic concentration range was not experimentally resolvable in comparison to electronic noise.

SUMMARY OF THE INVENTION

The present invention provides a micro sensor for monitoring the cleaning and drying processes for high aspect ratio micro channels in dielectric films oriented parallel to the fluid-solid interface during the manufacture of ICs, MEMS and other micro devices. The micro sensor can be used to monitor "vertical" micro features common in microelectronics fabrication or "horizontal" micro features found in MEMS or microfluidic fabrication. By forming the micro channels substantially parallel to the interface, the channels can be made with much higher and well controlled aspect ratios. In addition, the sensor can be configured to sense the impedance at various points along the micro features. The addition of a guard reduces the effects of any parasitic capacitance, which extends the measurement bandwidth of the sensor.

This is accomplished with a micro sensor comprising at least one and suitably several micro channels formed in a second dielectric layer between first and third dielectric layers and oriented substantially parallel to the sensor fluid-solid interface. Each micro channel has at least one opening through the third dielectric layer for receiving fluid. At least one and suitably several pairs of electrodes in the first and third dielectric layers are adapted to receive a measurement signal to measure the impedance of the micro channel between the electrodes. The micro sensor is suitably supported by a substrate having a covering dielectric layer. A capping dielectric layer is formed over the micro sensor to avoid direct contact between the fluid and the top electrode In another embodiment, multiple micro channels lie between the first and second dielectric layers. The micro channels may be identical or may have different geometries such as aspect ratio. The micro channels have an aspect ratio greater than 1-to-1 (length-to-width), typically greater than 10-to-1 and may exceed 100-to-1. Because the micro channels are formed in the plane of the dielectric there is really no limit on their length, hence aspect ratio.

In another embodiment, multiple electrode pairs can be used to measure the impedance of the micro channel(s) at different distances from the opening to more completely characterize residue in the micro channel.

In another embodiment, the same electrode pair may be used to measure an average impedance of multiple micro channels to get a better statistical measure of the impedance.

In another embodiment, at least some of the micro channels are filled with a porous dielectric material. The porous dielectric material is suitably a different material than the material in the first and second dielectric layers. Furthermore, different channels may be filled with different materials or the same material with different porosity.

In yet another embodiment, the sensor includes at least one conductive guard in at least one of the covering and capping dielectric layers whose voltage closely tracks the voltage of at least one of the first and second electrodes to shield the electrodes from the surrounding environment and thereby reduce the loss of measurement signal through the parasitic capacitance. At least one buffer supplies current to the at least one conductive guard so that the guard voltage closely tracks the electrode voltage without loading the measurement signal.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 5*a* through 5*i* are section views of a process for fabricating the micro sensor shown in FIG. 2;

DETAILED DESCRIPTION OF THE INVENTION

The present invention provides a micro sensor for monitoring the cleaning and drying processes for high aspect ratio micro features in dielectric films during the manufacture of ICs, MEMS and other micro devices. The term "micro feature" is used to refer to both "horizontal" and "vertical" (with respect to the substrate) void micro features such as trenches, vias, holes, pores, etc. These void micro features have aspect ratios of greater than 1:1, typically at least 3:1 and potentially much larger. The micro feature may be filled with a porous dielectric material as well.

The term "micro channel" is used to refer to the void micro structure formed parallel to the fluid-solid interface that is used to emulate and thus monitor in-situ micro features in semiconductor, MEMS and microfluidic devices. By forming the micro channels substantially parallel to the interface, the channels can be made with much higher and well controlled aspect ratios. The aspect ratio of a micro channel is the ratio of the depth of the micro channel (the distance it penetrates into the material away from the channel opening) to its width (the minimum distance across the channel opening, typically the thickness of the dielectric layer in which the micro channels are formed). Generally, the micro channels are formed parallel to the fluid-solid interface. This means that the materials (electrode and dielectric) between the micro channel and the fluid have a uniform thickness. However, variations in thickness of these layers may occur (accidental or intentional). Such variations in thickness are allowable: They do not impede the correct functioning of the sensor and they do not result in any benefit. In addition, the sensor can be configured to sense the impedance at various points along the micro features, allowing measurement of the impedance at various depths. The addition of a guard reduces the effects of any parasitic capacitance, which extends the measurement bandwidth of the sensor.

Figure 1:
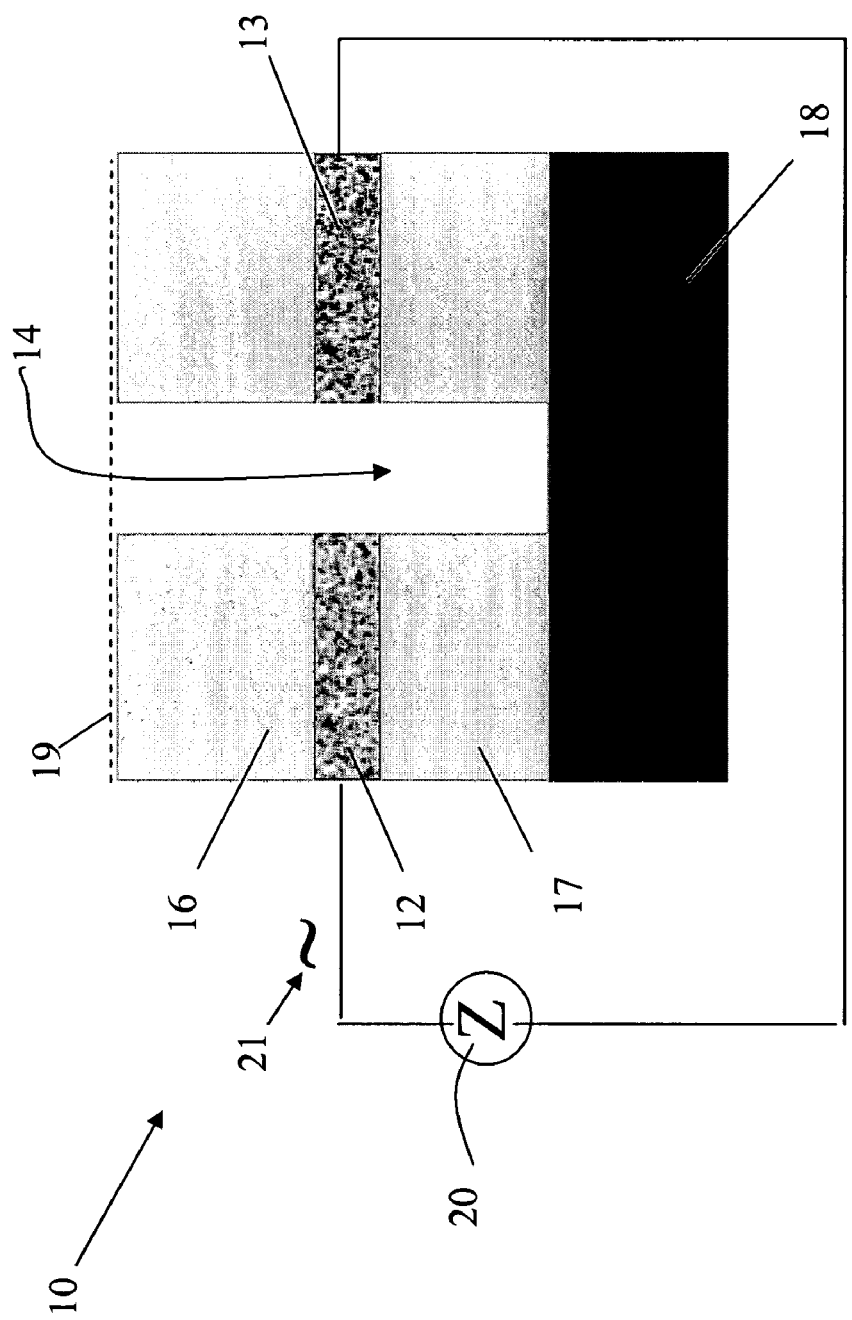
FIG. 1, as described above, is a section view of a known micro sensor for high aspect ratio structures in dielectric films.
Figure 2A:
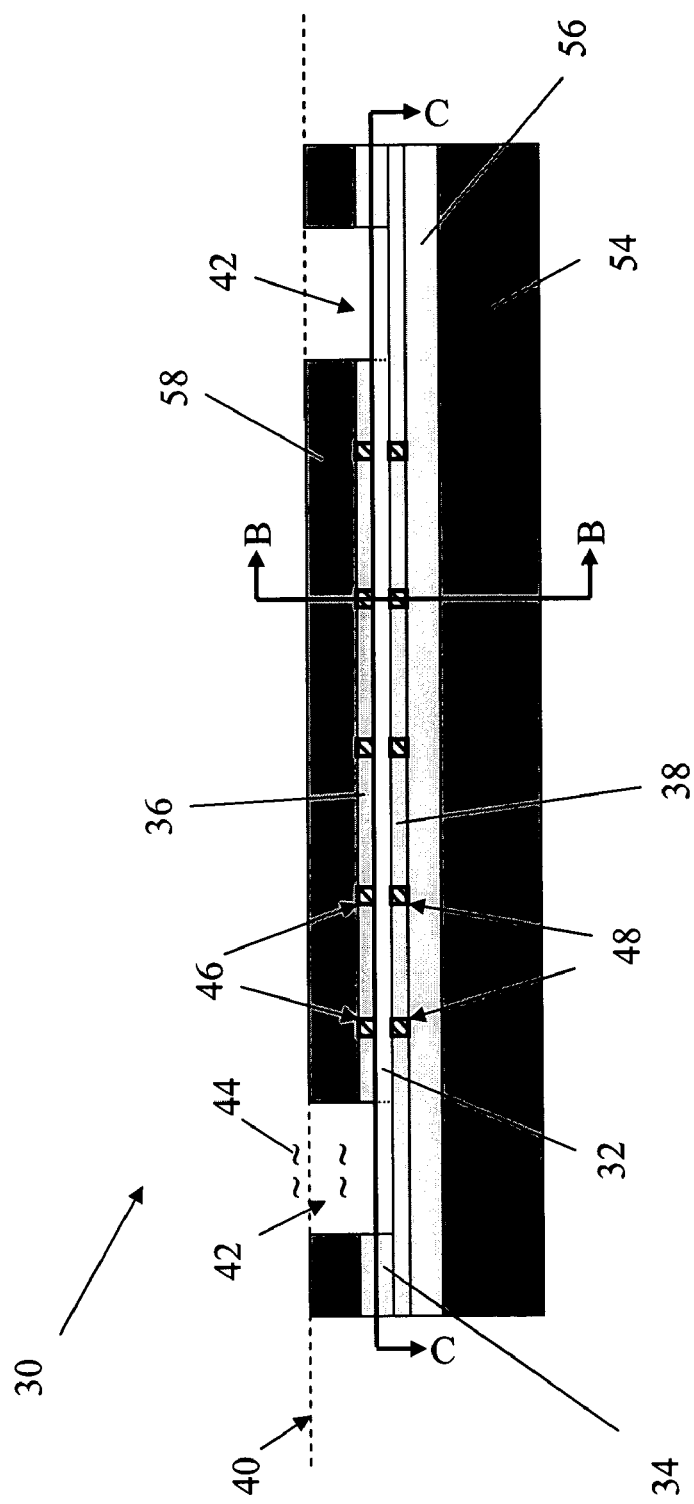
FIGS. 2*a* through 2*c* are section and plan views of a micro sensor having high aspect ratio micro channels formed parallel to the fluid-solid interface in accordance with the present invention.
Figure 2B:
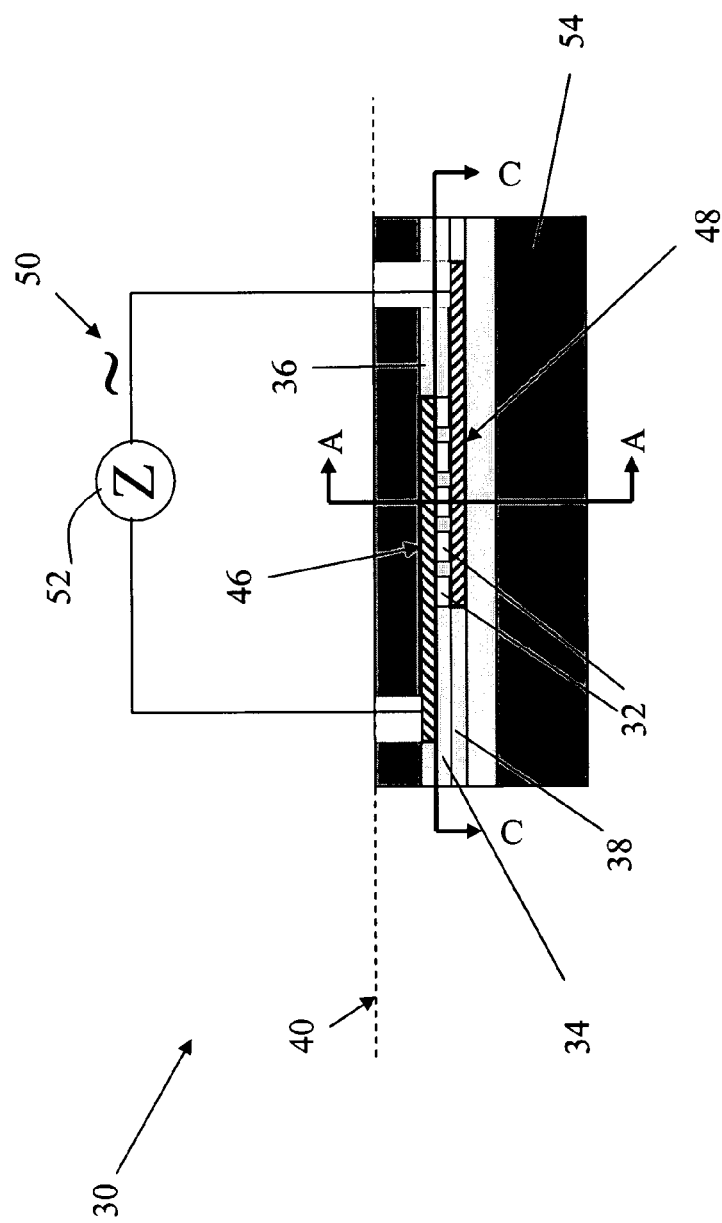
Figure 2C:
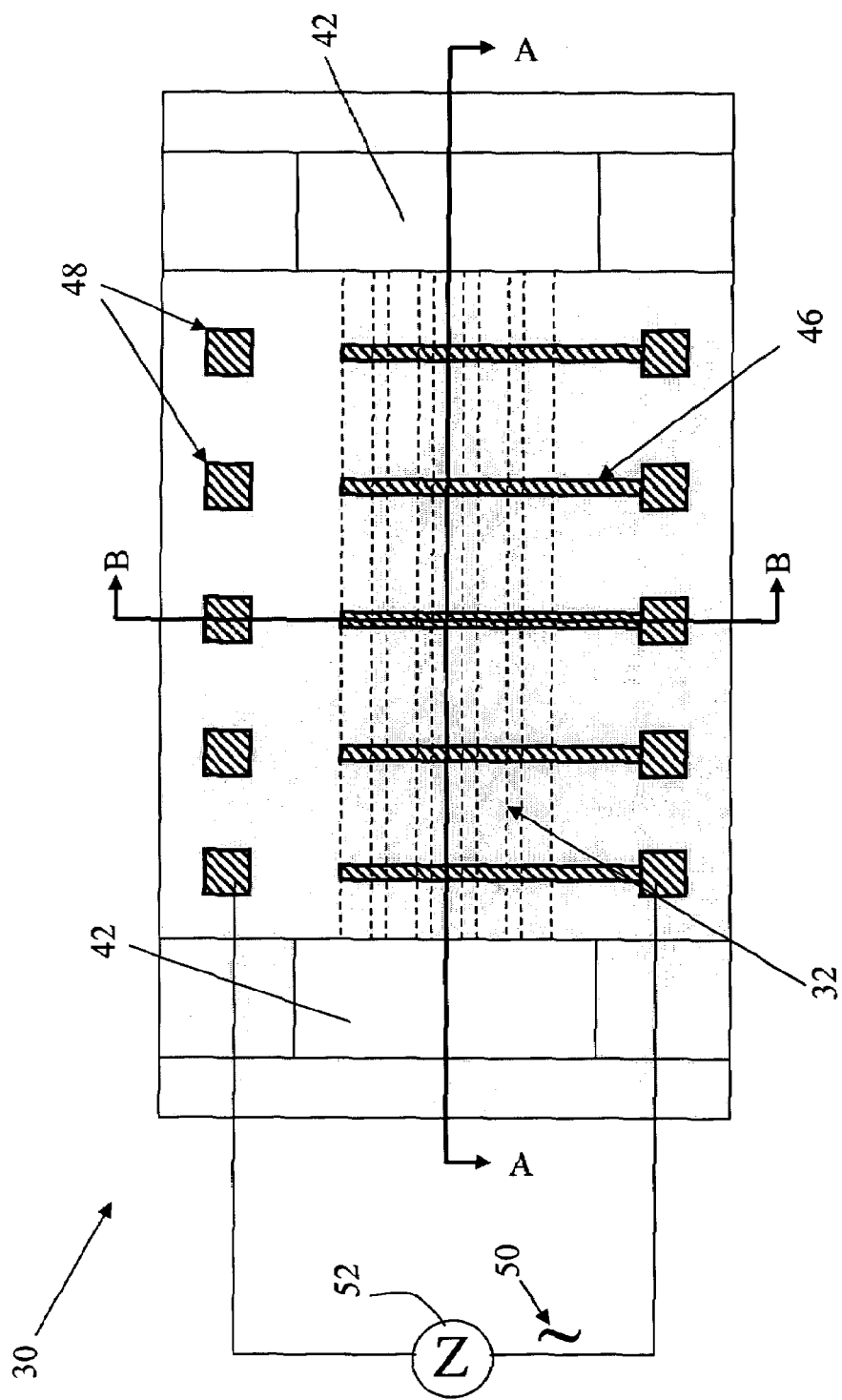

As shown in FIGS. 2a, 2b and 2c, an exemplary embodiment of a micro sensor 30 for monitoring the process of cleaning, rinsing and drying of micro features in-situ comprises at least one and suitably several micro channels 32 in a dielectric layer 34 between dielectric (e.g., silicon dioxide ($SiO_2$), silicon nitride ($Si_3N_4$) and low-K organic materials) layers 36 and 38 and oriented substantially parallel to the dielectric stack and sensor's fluid-solid interface 40. At least one and suitably several pair of electrodes 46, 48 (e.g., Poly-Si, Aluminum or copper) in dielectric layers 36 and 38, respectively, are adapted to receive a measurement signal 50 and carry the measurement signal (voltage and current) to the micro channel. An impedance analyzer 52 measures the impedance of the micro channel between the electrodes (ratio of voltage and current and phase difference between the voltage and current). The micro sensor is suitably supported by a substrate 54 (e.g. a silicon wafer or a glass slide) having a covering dielectric layer 56. If the substrate is itself a dielectric the covering dielectric may be omitted. A capping dielectric layer 58 is formed over the micro sensor to avoid direct contact between the fluid and the electrode 46. Each micro channel has at least one opening and suitably two openings 42 through the dielectric layers 36, 58 between the channel 32 and the fluid-solid interface 40 for receiving fluid 44.

As shown, the micro sensor may be configured with multiple micro channels 32 to improve the reliability of the impedance measure. The micro channels are suitably identical but may have different geometries such as length (the maximum distance across the channel opening) and depth. If the micro channels have different depth, then complex mathematical deconvolution must be performed to determine the contribution of each channel length to the total impedance. Hence, unless the mathematical form of the dependence of impedance on depth is well-understood, it is not desirable to include micro channels of different depth in the same sensor. The micro channels have an aspect ratio greater than 1-to-1 (depth-to-width), typically greater than 3-to-1 and may exceed 100-to-1. Because the micro channels are formed in the plane of the dielectric there is really no limit on their depth, hence aspect ratio.

In order to get a more complete characterization of the residue in the micro channel, multiple electrode pairs 46, 48 can be used to measure the impedance of the micro channel(s) at different distances from the opening 42. The same electrode pair 46, 48 may be used to measure the impedance of multiple identical micro channels 32 to reduce the measurement noise by placing the micro channels in parallel.

In an alternate embodiment, at least some of the micro channels 32 are filled with a porous dielectric material. The porous dielectric material is suitably a different material than the material in the dielectric stack. Furthermore, different micro channels may be filled with different materials or the same material with different porosity. In that case, the pores fill with fluid (i.e. the porous material is soaked) and the sensor's electrical response is indicative of the residual contamination inside the pores in the porous material.

Figure 3:
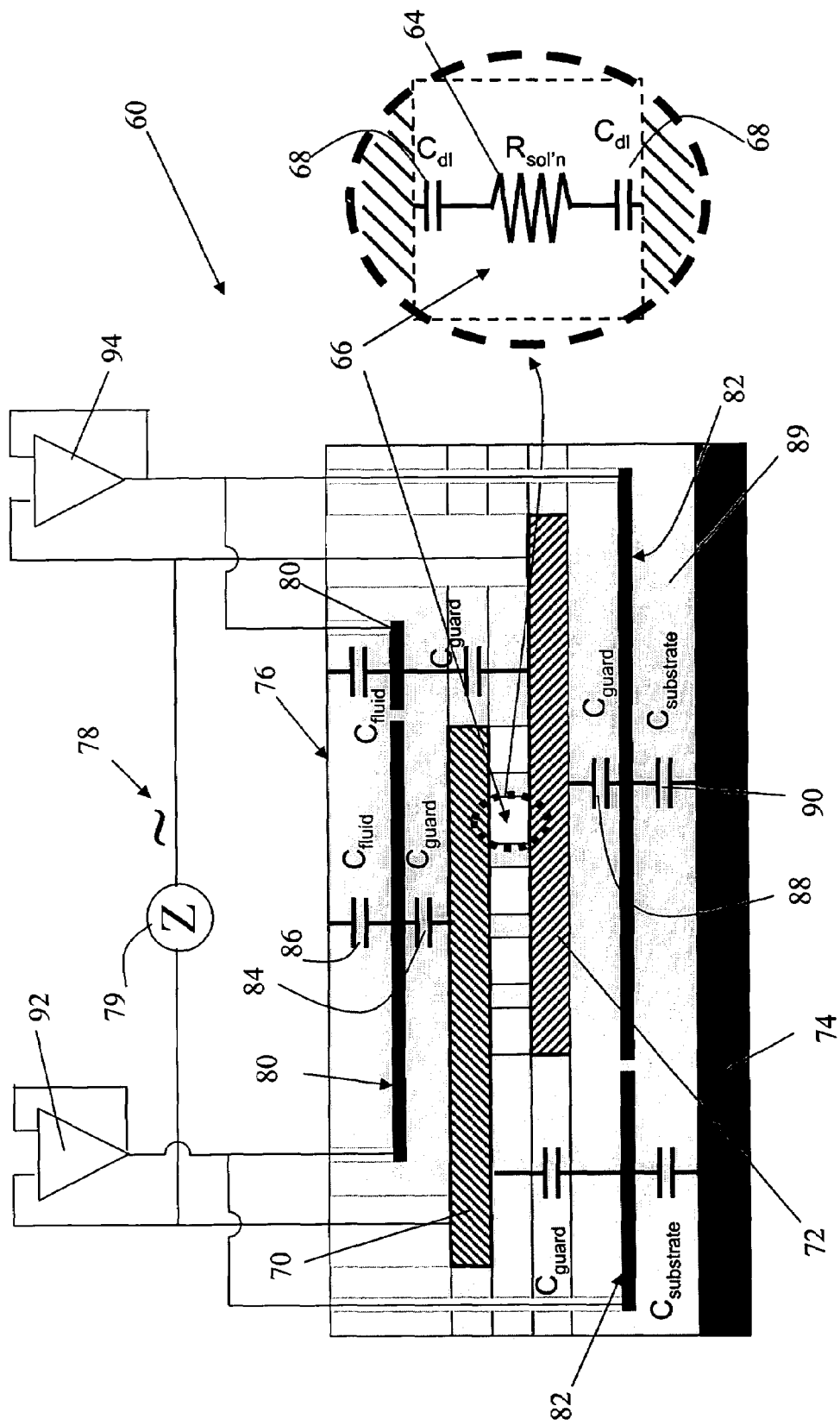
FIG. 3 is a section view and partial schematic of the micro sensor including a guard for shielding the sensor's electrodes to reduce the effects of parasitic capacitance.

The addition of a conductive guard reduces the loss of the measurement voltage to parasitic capacitance between the electrodes and the substrate or fluid, which extends the measurement bandwidth of the sensor. The equivalent circuit diagram of a micro sensor 60 with a guard is shown in FIG. 3. The sensor is configured to measure the solution resistance $R_{sol'n}$ 64, (of which there can be several in parallel—when there are multiple micro channels in parallel) which is dependent on the ionic concentration of impurities in the fluid inside the micro channel 66. At solid-solution interfaces, an interface double layer forms because charges in the solution that are mobile (ions) respond to the presence of fixed charges on the solid. The interface double layer is responsible for a capacitance $C_{dl}$ 68 between the electrode and the solution, which forms an impedance $Z_{dl}=1/j\omega C_{dl}$ where $\omega$ is the measurement signal 78 radial frequency in series with $R_{sol'n}$.

Since the sensor 60 measures the solution resistance through two series capacitors, the measurement must be performed using an ac signal. If the series impedance $Z_{dl}$ is much larger than $R_{sol'n}$, (i.e. if $C_{dl}$ is small and/or the measurement radial frequency $\omega$ is small so that $R_{sol'n} \ll 1/\omega C_{dl}$), then the sensor's impedance output is dominated by $C_{dl}$ and the solution resistance $R_{sol'n}$ can not be effectively measured.

Electrodes 70, 72 also have parasitic capacitances with other conductors in their neighborhood. The total parasitic capacitance is primarily between the electrodes 70, 72 and the substrate 74. There can also be significant capacitance between the electrodes 70, 72 and the fluid above the sensor's fluid-solid interface 76. The parasitic capacitances form parasitic shunt circuits across the solution resistance. These shunt circuits are in parallel with the solution resistance and therefore allow the measurement signal 78 to bypass the solution resistance 64. If the shunt impedance is significantly lower than the solution resistance, then the sensor's impedance output as measured by impedance analyzer 79 is dominated by the parasitic capacitances and the solution resistance can not be effectively measured.

For the sensor to be useful as a monitor of the fluid in the micro feature, the total parasitic capacitance must be sufficiently small to allow an electrical measurement of the total impedance between the electrodes to resolve $R_{sol'n}$ and/or $C_{dl}$. If the parasitic capacitance dominates the total electrical response, then the circuit will not have a good signal to noise ratio and the sensor will not be very sensitive. If the parasitic capacitance dominates, the equivalent circuit calculation predicts no discernable impedance variation between highest and lowest solution resistances. To mitigate this parasitic capacitance, it can be beneficial to include guards 80 and 82 that shield electrodes 70 and 72, respectively. A guard is an additional conductor that divides the dielectric between an electrode and the substrate and/or the electrode and the fluid into two parts that form two new capacitors, $C_{guard}$ 84 and $C_{fluid}$ 86 or $C_{guard}$ 88 and $C_{substrate}$ 90. $C_{guard}$ is the capacitor between the electrode and the guard. $C_{fluid}$ is the capacitor between the guard and the fluid. $C_{substrate}$ is the capacitor between the guard and the substrate. If $C_{substrate}$ is small so that $\omega C_{substrate} \ll 1/R_{sol'n}$, (e.g. the substrate 74 is relatively thick and made of dielectric or the substrate covering dielectric layer 89 is relatively thick), then guard 82 may be omitted. If $C_{fluid}$ is small so that $\omega C_{fluid} \ll 1/R_{sol'n}$ (i.e. if the capping layer dielectric 58 is thick), then guard 80 may be omitted.

The guards are biased so that their voltages follow as closely as possible the respective electrode voltages at all times, even when the electrode voltage changes over time. The guard voltage need only track the ac component of the electrode voltage but suitably tracks the total instantaneous electrode voltage. The current required to make the guard voltage the same as the electrode voltage is supplied by buffers 92 and 94, e.g. an operation amplifier (OpAmp), not by the measurement signal 78. The Buffer reproduces the desired voltage without significant loading it. Since the voltage difference between the electrode and its guard is several orders of magnitude lower than the voltage difference between the electrode and other conductors in the neighborhood of the sensor (substrate and fluid), the loss or distortion of the measurement signal through the parasitic capacitance $C_{guard}$ will be very, very small. The measurement signal is not affected by the capacitors $C_{fluid}$ and $C_{substrate}$ because the measurement signal is buffered prior to being applied to the guard. $C_{fluid}$ and $C_{substrate}$ must be charged and discharged by the guard buffer.

Figure 4:
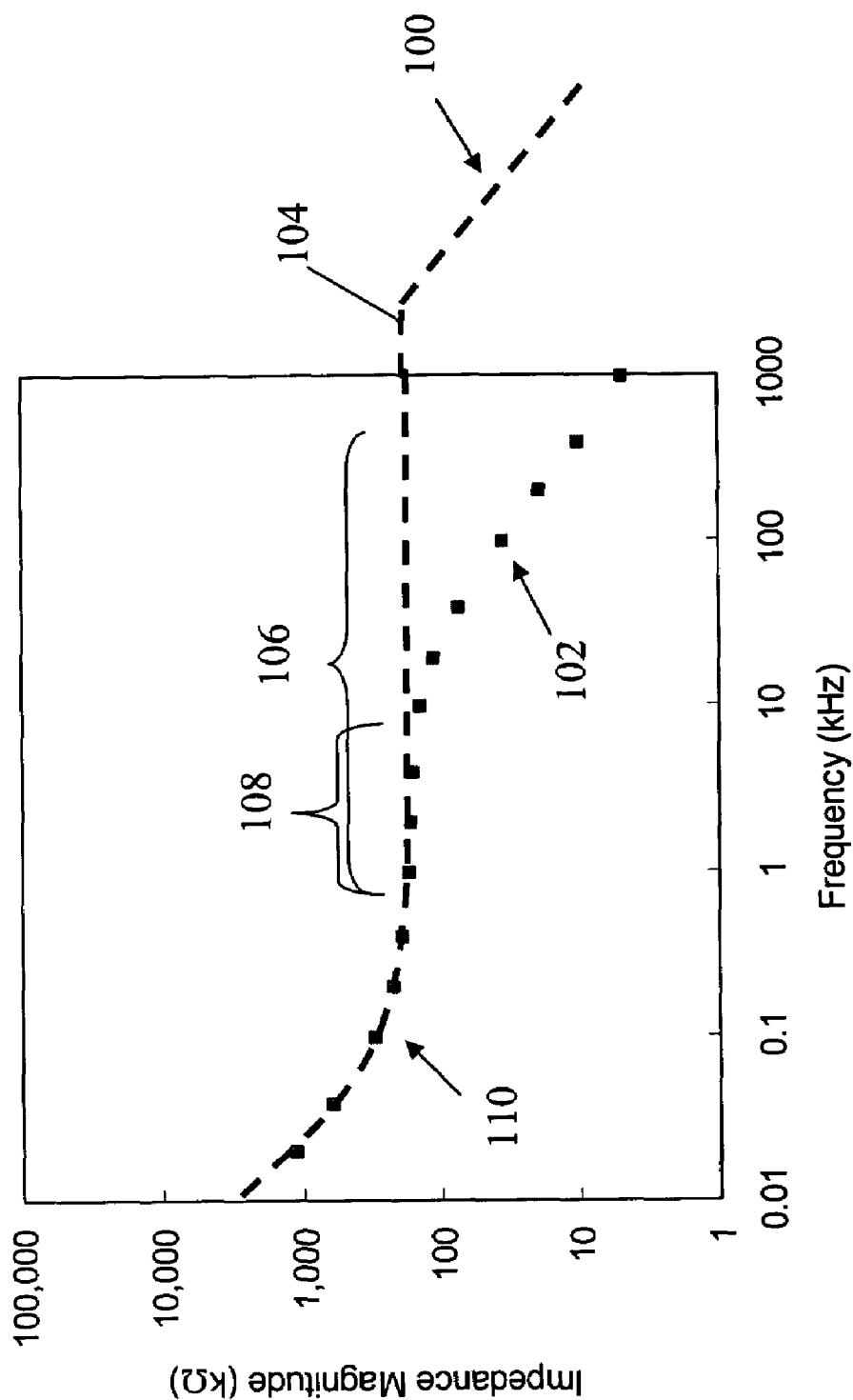
FIG. 4 is a calibration plot of impedance vs. frequency for the micro sensor illustrating the frequency extension achieved by the presence of the guard.

FIG. 4 is a plot of the micro sensor's frequency response 100 with a guard and 102 without a guard. With a guard, the loss or distortion of the measurement signal through the parasitic capacitance will be very, very small. This makes the impedance of the shunt path (the path the signal must take to bypass the micro feature) that limits the high frequency operation much larger. The net effect is to shift the high frequency limit 104 of the measurement to much higher frequencies so that the useful measurement region 106 with a guard is much wider than the useful measurement region 108 without a guard. The smaller the fraction of the electrode that is covered by the guard, the lower the frequency 104 that high frequency roll-off will occur.

It is desirable to make the electrode as small as possible to reduce the sensor's manufacturing cost. The frequency at which low frequency roll-off occurs 110 is determined by the capacitance $C_{dl}$ and resistance $R_{sol'n}$. In the absence of a guard, the frequency at which high frequency roll-off occurs 104 is determined by the total parasitic capacitance (the sum of the capacitance between the electrode and the substrate and between the electrode and the fluid) and the resistance $R_{sol'n}$. Reducing the active electrode area (area of the electrode that is exposed to the fluid inside the micro feature) reduces $C_{dl}$, which increases the frequency at which low frequency roll-off occurs. In the absence of a guard, reducing the electrode active area does not increase the frequency at which high frequency roll-off occurs as much as the low frequency roll-off. Hence reduction of the electrode active area will tend to bring the low frequency roll-off and the high frequency roll-off closer together. If the electrode active area is reduced too much (causing the high frequency roll-off and low frequency roll-off to overlap), accurate measurement of $R_{sol'n}$ is no longer possible. Hence reducing the size of the electrode is limited if there is no guard. A guard allows the high-frequency roll-off to be extended to higher frequencies without penalty to the low frequency roll-off. The low frequency roll-off can therefore be allowed to increase in frequency by reducing the size of the sensor.

The signal to noise ratio of the micro sensor without the guard is determined by the geometry of the sensor and the materials choice. The signal to noise ratio of the micro sensor with the guard is not determined by the parasitic elements, but by the accuracy of the electronics used to measure the trench impedance. The micro sensor with guard can therefore measure the micro feature impedance more accurately in a noisier environment.

For rinsing applications, the presence of ionic contaminants in ultra pure water changes the resistivity of the water even if very small concentrations (parts per billion level) are present. Therefore, the impedance measured between two electrodes will depend very much on the conductivity of the fluid and thus the presence of ions. Even non-ionic impurities, directly and through interactions with other species present, change the dielectric properties inside the micro feature, which in turn define the impedance. For drying applications, the removal of the water from the micro feature (replacing it with air, pure nitrogen or some other gas) will likewise result in a measurable change in impedance, since the difference between the conductivity of ultra pure water and air can easily be detected. Conduction along sidewalls can be measured, so that the amount of moisture adsorbed on the sidewalls or (slightly) conducting residual impurities on the sidewalls will be detected.

The micro sensor measures resistivity inside the micro feature, not in the bulk of a fluid. Bulk properties are often irrelevant both in terms of the amount and also the rate of change. This means that the sensor is placed "adjacent to" the micro feature that needs to be monitored for cleaning or drying to monitor the "inside" of the micro feature. The capability to perform in-situ measurements is why it is so important to be able to reduce the size of the micro sensor without sacrificing performance.

Furthermore, micro sensor measures the full impedance spectrum, of which the resistivity is just a part (impedance is a complex number quantity that is dependent on frequency while resistance is the real part of the dc value of the impedance). This means that a large amount of other information, such as the dielectric absorption and frequency dependence is also available. The sensor can monitor specific ionic species and or non-ionic species (since these change the permittivity and surface adsorption). Because trace quantities of impurities can result in significant change in conductance or dielectric constant and because these electrical properties can be accurately measured, the sensitivity of the sensor is very good.

An exemplary process for fabricating a particular micro sensor 30 with multiple micro channels parallel to the sensor's fluid-solid interface as shown in FIG. 2 is illustrated in FIGS. 5a through 5i.

Figures 5A, 5B:
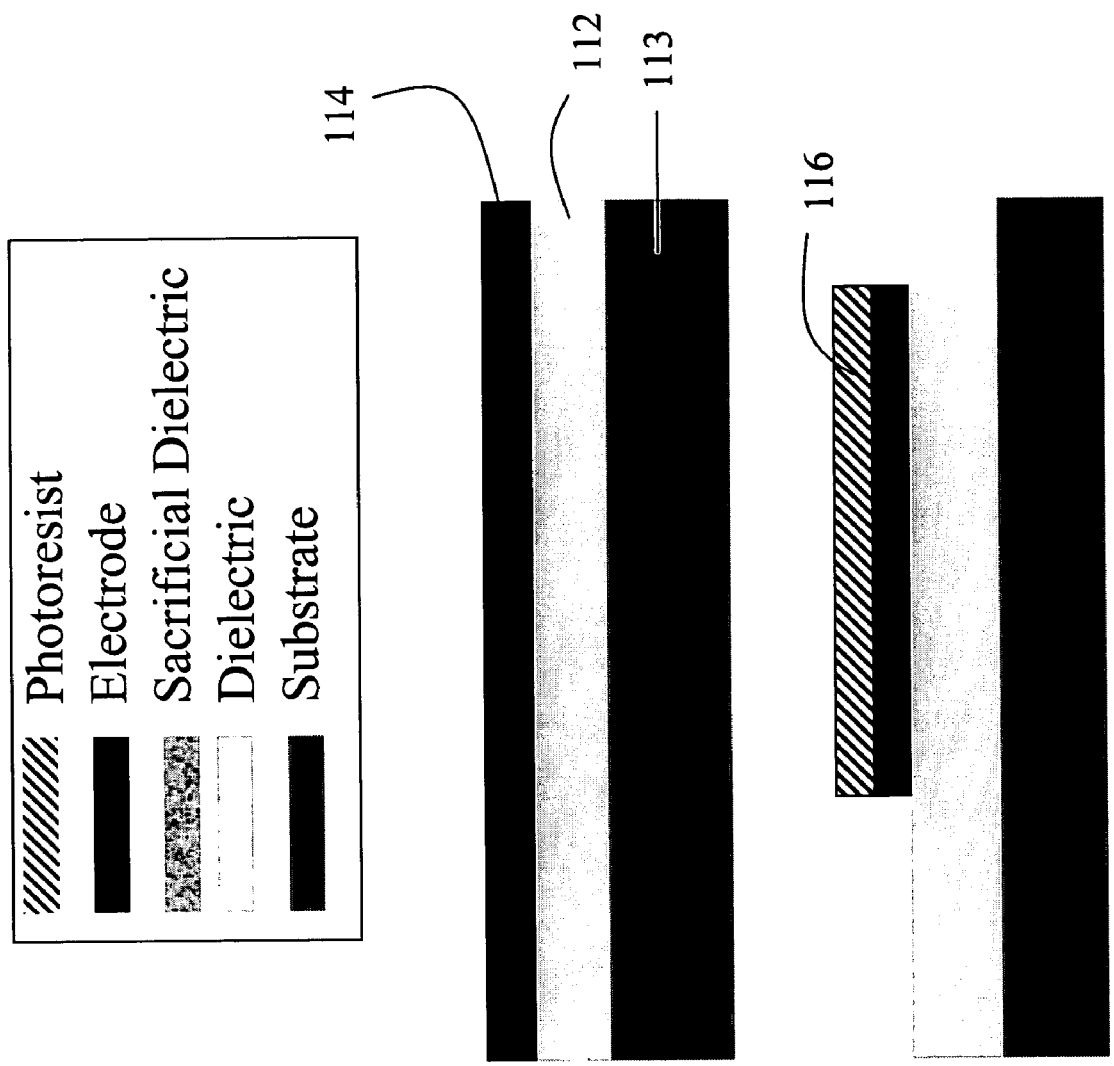

As shown in FIG. 5a, a covering dielectric 112 such as $Si_3N_4$ is deposited with a typical thickness of about 3 µm on a substrate 113, which can be silicon, $Si_3N_4$, glass or a similar inert material. Optionally, if the substrate itself is a dielectric such as $Si_3N_4$, this step may be omitted. A conductor 114 such as copper or doped polysilicon with typical thickness of 0.5 µm is deposited on dielectric 112 and will form part of the bottom electrode 48 as shown in FIG. 2a and FIG. 2b.

As shown in FIG. 5b, a photoresist 116 is deposited on conductor 114 and the pattern of the bottom electrode (48 shown in FIG. 2b) is defined using photolithography and chemical etching.

As shown in FIG. 5c, the photoresist is removed and a first dielectric 118, such as $Si_3N_4$ is deposited with a typical thickness of 1 µm on top of the conductor (114 as shown in FIG. 5b). The dielectric is made planar by polishing until the conductor is just exposed.

As shown in FIG. 5d, a second dielectric 119, such as $Si_3N_4$, is deposited with a typical thickness of 0.1 µm. This thickness will ultimately be the width of the micro channel. The second dielectric is patterned to open the micro features 120 (which will become micro channels 32 in FIG. 2a and FIG. 2b and the bottom portion of the opening 42 in FIG. 2a) using photoresist deposition, photolithography and chemical etching. The width of micro features 120 will ultimately be the length of the micro channel. The photoresist is then removed.

Figure 5F:
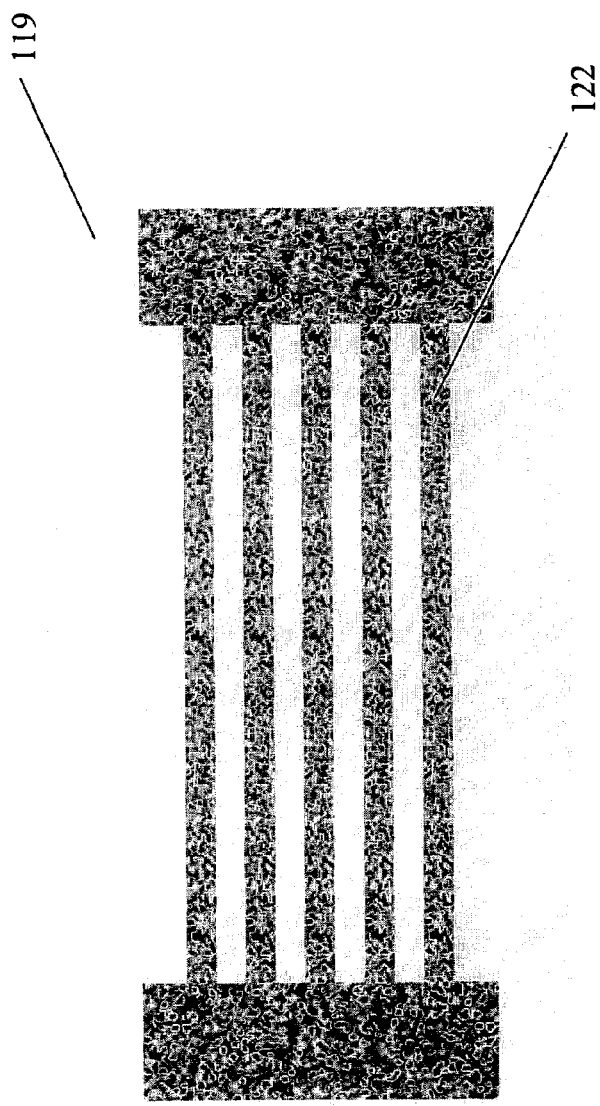

As shown in FIG. 5e, a sacrificial dielectric 122, such as $SiO_2$, is deposited on top of the patterned second dielectric 119 with a typical thickness of 0.3 µm. The dielectric is made planar by polishing until the second dielectric (119 in FIG. 5d) is just exposed. The plan view showing the section D-D in FIG. 5e at this point in the manufacturing process is shown in FIG. 5f.

Figure 5G:
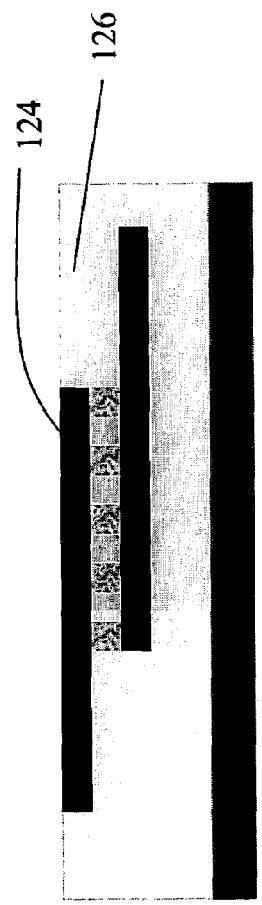

As shown in FIG. 5g, a conductor 124 such as copper or doped polysilicon with typical thickness of 0.5 µm is deposited (on dielectric 119 in FIG. 5d and 122 in FIG. 5e). This conductor will form part of the top electrode 46 as shown in FIG. 2a and FIG. 2b. A photoresist is deposited on conductor 124 and the pattern of the top electrode (46 shown in FIG. 2a and FIG. 2b) is defined using photolithography and chemical etching. The photoresist is removed and a third dielectric 126, such as $Si_3N_4$ is deposited with a typical thickness of 1 µm on top of the patterned conductor 124. The dielectric is made planar by polishing until the conductor 124 is just exposed.

Figure 5H:
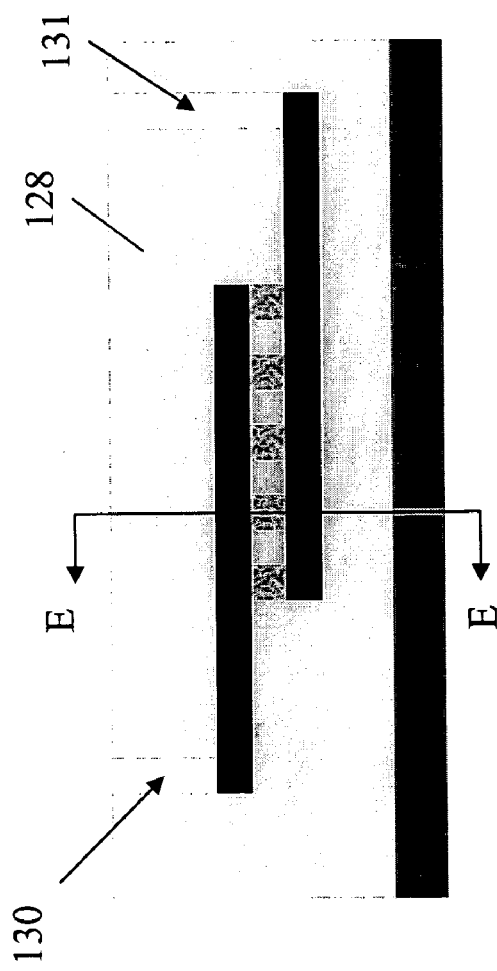
Figure 5I:
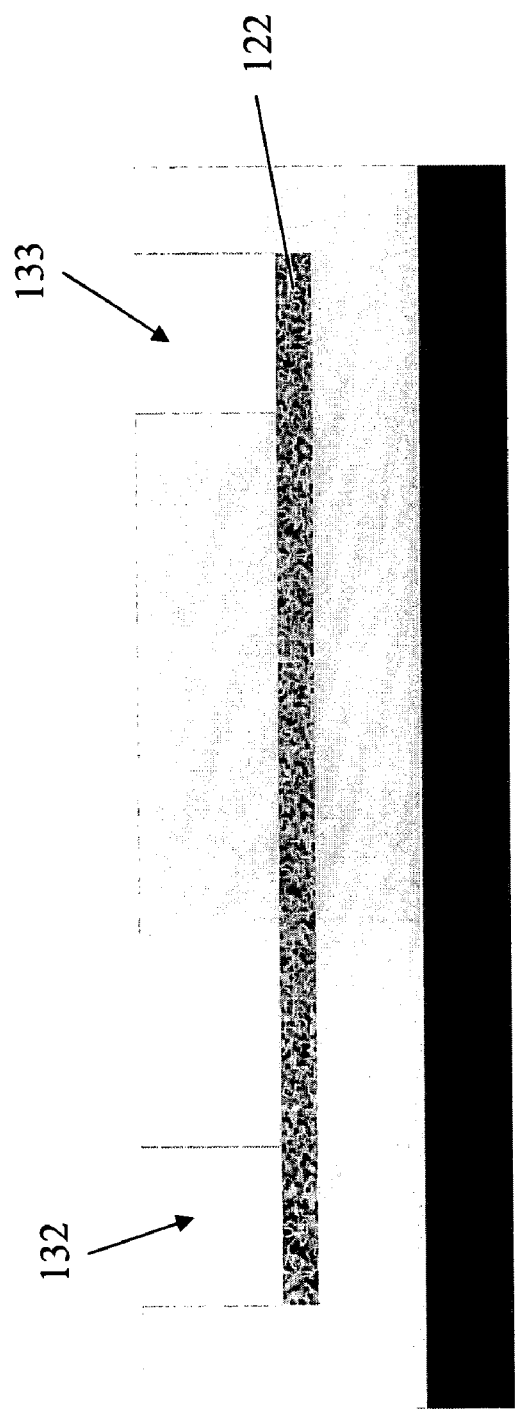

As shown in FIG. 5h, a capping dielectric 128, such as $Si_3N_4$ is deposited with a typical thickness of 5 µm on top of the patterned conductor and third dielectric. A photoresist is deposited on the dielectric 128 and the pattern of the electrical contact openings 130 and 131 to the two electrodes and the openings for fluid entrance into the micro channels are defined using photolithography and chemical etching. The photoresist is removed. The cross section view across the cutline E-E, showing openings 132 and 133 for the fluid to the micro channels at this point in the process is shown in FIG. 5i.

The sacrificial dielectric layer (122 shown in FIG. 5e, FIG. 5f and FIG. 5i) is removed by chemical etching (e.g. by immersing the structure in HF) to complete the fabrication.

Figure 6:
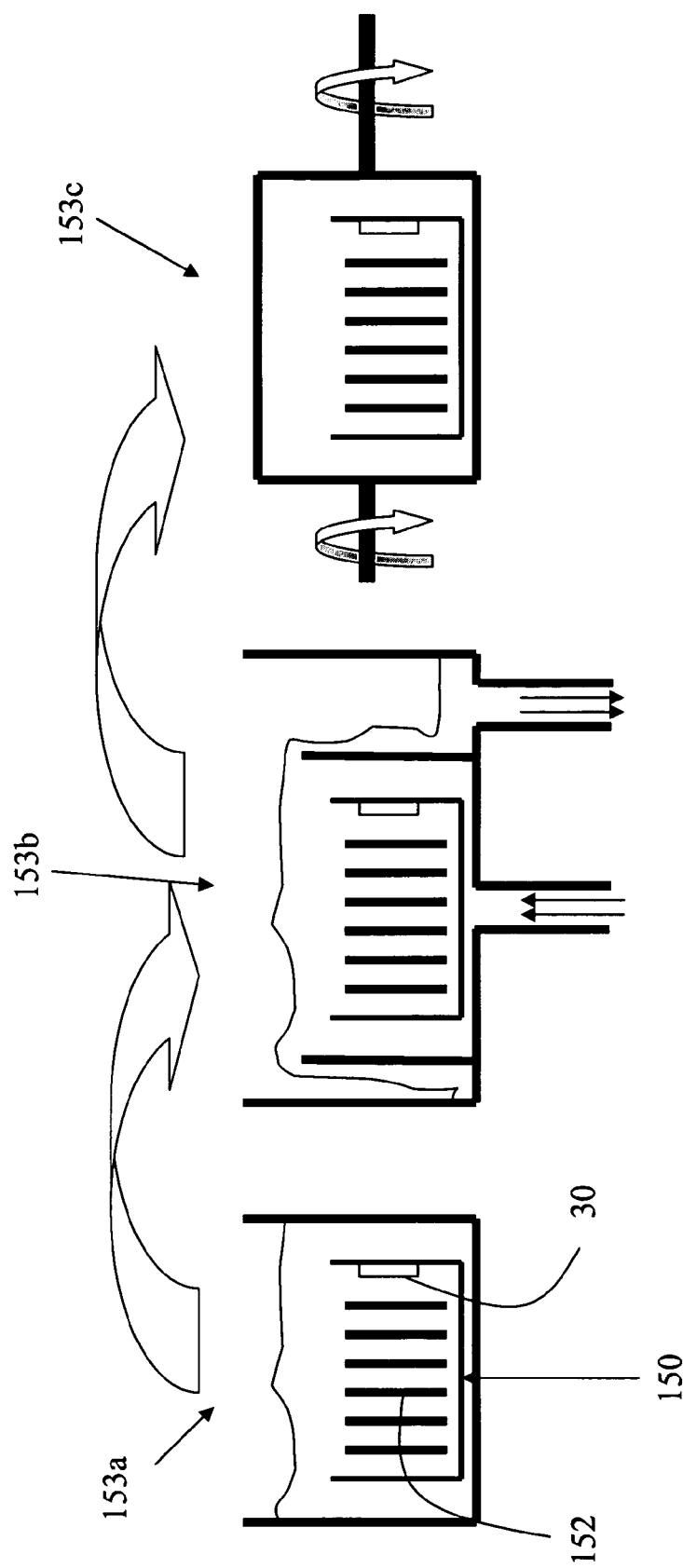
FIG. 6 is a diagram of a clean/rinse/dry process using the micro sensor.
Figure 7:
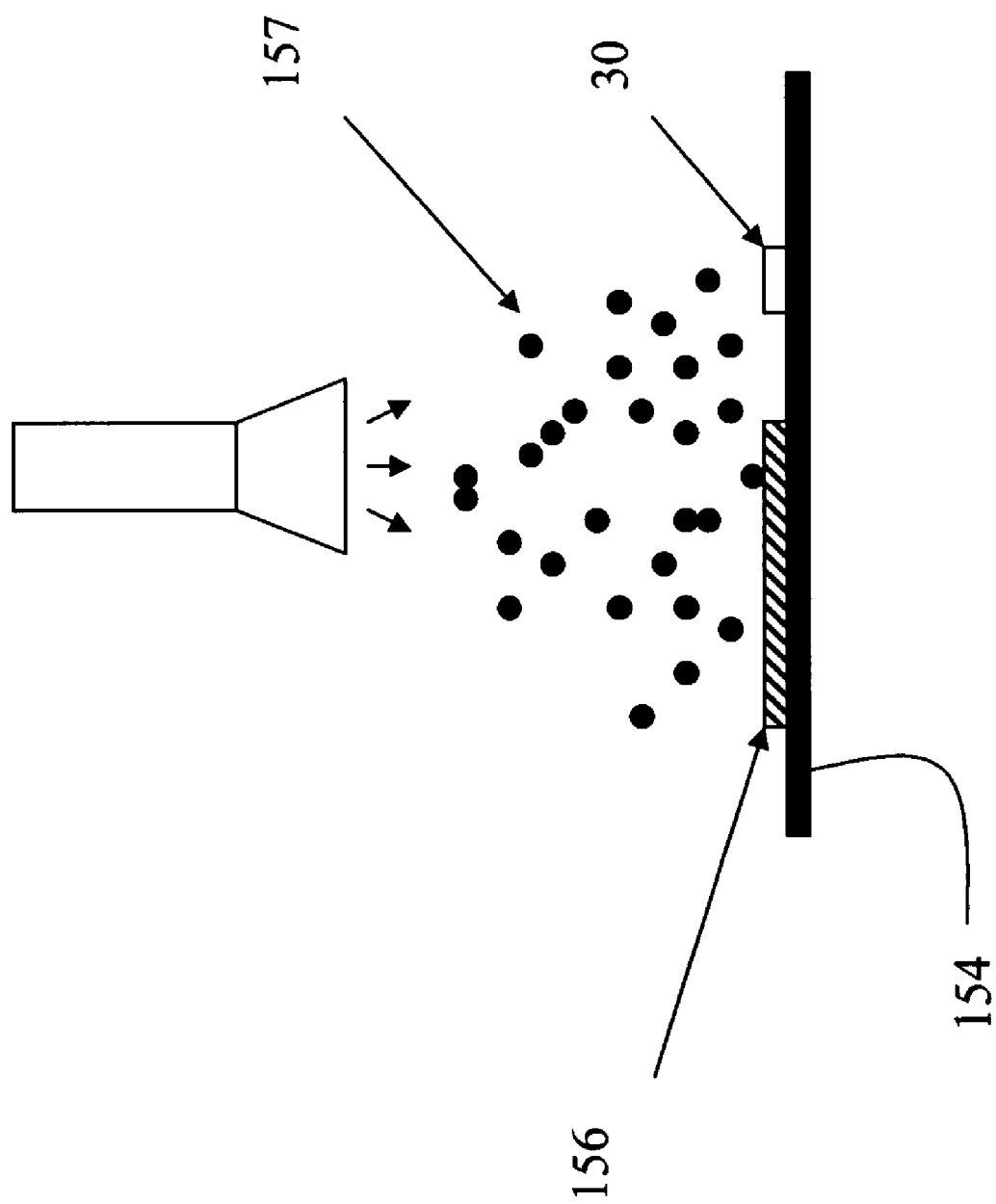
FIG. 7 is a diagram of an alternate clean/rinse/dry process using the micro sensor.
Figure 8:
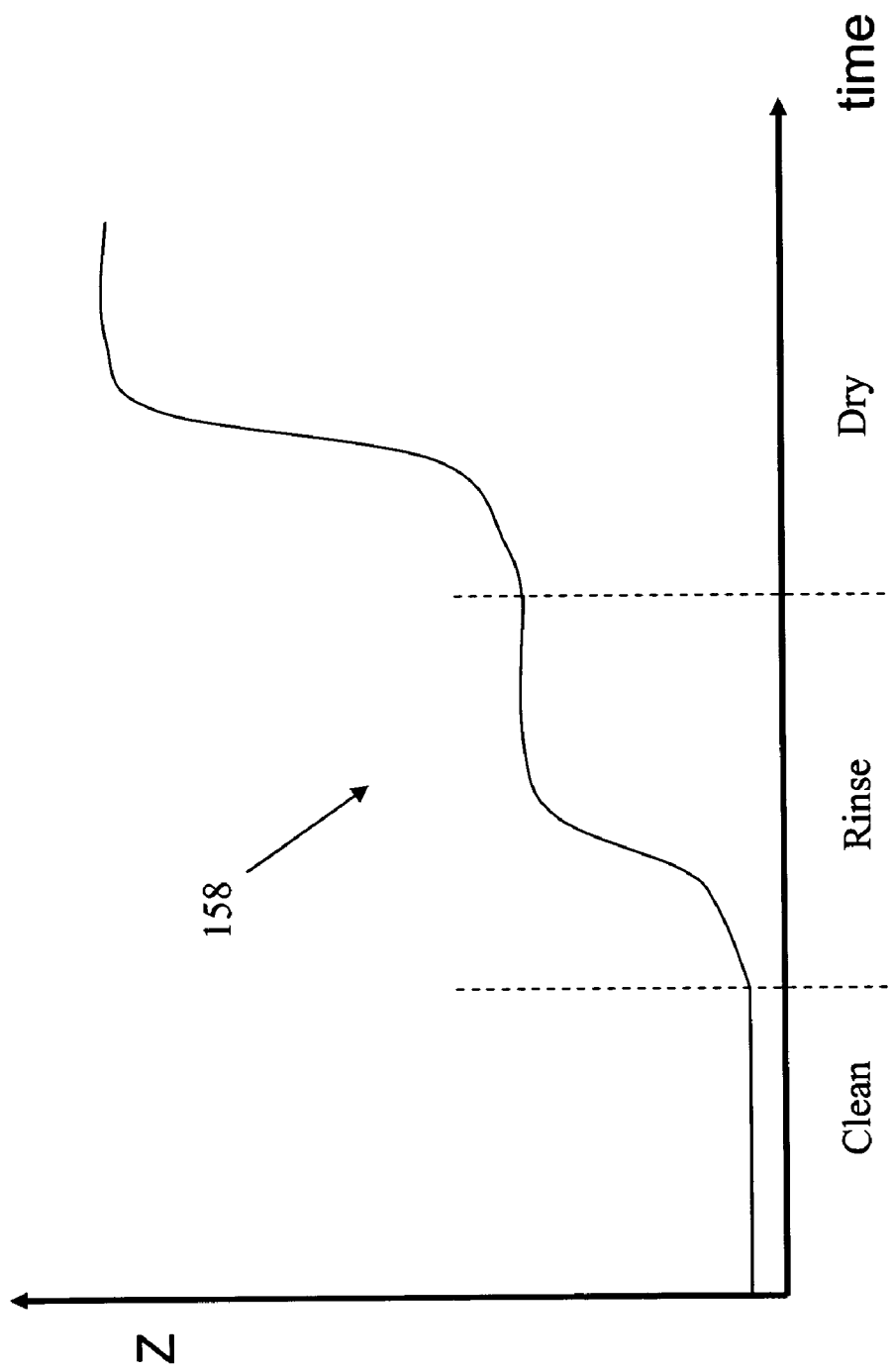
FIG. 8 is a plot of impedance vs. time for a representative clean/rinse/dry cycle.

The use of the micro sensor 30 to monitor the clean/rinse/dry process is illustrated in FIGS. 6-8. Typically, micro sensor 30 would be placed in a cleaning solution of a known ion concentration to calibrate the sensor. Once calibrated the micro sensor may be inserted in a cassette 150 with a number of other product wafers 152 and processed through a sequence of clean/rinse/dry baths 153a-153c as shown in FIG. 6 or mounted on a chuck 154 with a single wafer 156 and subjected to a sequence of clean/rinse/dry sprays 157 as shown in FIG. 7.

As shown in FIG. 8, as the micro sensor passes through the clean/rinse/dry cycle the measured impedance 158, of one electrode pair or averaged over several pair, changes fairly dramatically from a very low impedance during cleaning, to a moderate impedance during rinse and finally to a much higher impedance when the drying process is completed. By first calibrating the sensor to the allowable surface concentration, the rinse and dry process duration can be optimized. Also, by first calibrating the process and then monitoring the impedance during an actual production run, the wafers can be transferred from one process to the next to ensure adequate clean/rinse/dry without wasting time or chemicals. Alternatively, the sharp increases in impedance levels and subsequent leveling can be used to trigger a transfer to the next processing stage. If process calibration is both accurate and stable enough, e.g. the times to transfer, then it is possible that the micro sensor may not be needed during the actual production runs, but is merely used to periodically confirm that the process performance is still within specifications.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A micro sensor for electrochemically monitoring fluid residue, comprising:
   a substrate;
   first, second and third fixed dielectric layers in a stack on said substrate, said third dielectric layer having a top surface that defines a fluid-solid interface for receiving a fluid;
   a buried micro channel in the second dielectric layer between the first and third dielectric layers;
   at least one opening through the third dielectric layer to said buried micro channel allowing the fluid at said fluid-solid interface to enter the buried micro-channel; and
   at least one pair of lower and upper electrodes in the first and third dielectric layers at a fixed separation and spaced a known distance from said at least one opening, said lower and upper electrodes exposed to fluid in the micro channel and configured to receive an ac measurement signal to measure the impedance of the micro channel between the electrodes as a measure of fluid residue in said micro channel at the known distance from the opening.

2. The micro sensor of claim 1, wherein a plurality of electrode pairs is spaced to measure the impedance of the micro channel and the fluid residue in said micro channel at different distances from said opening.

3. The micro sensor of claim 2, wherein a plurality of said micro channels lie in the second dielectric layer.

4. The micro sensor of claim 3, wherein each pair of electrodes is adapted to receive a measurement signal to measure an average impedance of a plurality of said micro channels.

5. The micro sensor of claim 1, wherein said substrate includes a covering dielectric layer beneath the first dielectric layer and further comprising a capping dielectric layer over the third dielectric layer and the electrode formed therein.

6. The micro sensor of claim 5, further comprising:
   an impedance analyzer that applies an ac measurement signal between the lower and upper electrodes to measure the impedance of the micro channel as the ratio between an ac measurement signal voltage and current;
   a first conductive guard in the cover dielectric layer between the lower electrode and the substrate;
   a first buffer having a first input connected to the impedance analyzer and a second input connected to a buffer output, said buffer having unity gain bandwidth larger than the ac measurement signal frequency to supply current to the first conductive guard so that its voltage closely tracks the ac measurement signal voltage applied to the lower electrode.

7. The micro sensor of claim 5, further comprising:
   an impedance analyzer that applies an ac measurement signal between the lower and upper electrodes to measure the impedance of the micro channel as the ratio between an ac measurement signal voltage and current;
   a first conductive guard in the capping dielectric layer between the upper electrode and the fluid-solid interface;
   a first buffer having a first input a first input connected to the impedance analyzer and a second input connected to a buffer output, said buffer having unity gain bandwidth larger than the ac measurement signal frequency to supply current to the first conductive guard so that its voltage closely tracks the ac measurement signal voltage applied to the upper electrode.

8. The micro sensor of claim 5, further comprising:
an impedance analyzer that applies an ac measurement signal between the lower and upper electrodes to measure the impedance of the micro channel as the ratio between an ac measurement signal voltage and current;
first and second conductive guards in the capping dielectric layer beneath the upper and lower electrodes respectively;
third and fourth conductive guards in the cover layer above the upper and lower electrodes respectively; and
first and second buffers each having a first input connected to the impedance analyzer and a second input connected to a buffer output, said buffers having unity gain bandwidth larger than the ac measurement signal frequency to supply current to the first and third and second and fourth conductive guards, respectively, so that their voltages closely track the ac measurement signal voltages applied to the upper and lower electrodes, respectively.

9. The micro sensor of claim 1, wherein the aspect ratio of the micro channel is greater than 10-to-1.

10. The micro sensor of claim 1, wherein the aspect ratio of the micro channel is greater than 100-to-1.

11. The micro sensor of claim 1, wherein the micro channel is filled with a porous dielectric material.

12. The micro sensor of claim 11, wherein the porous dielectric material is a different material than said second dielectric layer.

13. The micro sensor of claim 1, wherein there is only one said opening from the fluid-solider interface to the buried micro-channel to allow fluid to enter from the interface and exit to the interface.

14. The micro sensor of claim 13, wherein a plurality of electrode pairs is spaced to measure the impedance of the micro channel and the fluid residue in said micro channel at different distances from said one opening.

15. The micro sensor of claim 1, wherein first and second said openings in the third dielectric allow fluid to enter from the interface and exit to the interface.

16. The micro sensor of claim 15, wherein a first electrode pair is positioned towards said first opening, a second electrode pair is positioned towards said second opening, and a third electrode pair is positioned there between to monitor fluid residue in the micro channel at three different locations.

17. A micro sensor, comprising:
a substrate;
a dielectric on the substrate, said dielectric having a top surface that defines a fluid-solid interface for receiving a fluid;
a buried micro channel in the dielectric substantially parallel to and spaced below said fluid-solid interface;
at least one opening through the top surface of the dielectric to the buried micro channel for allowing the fluid to enter the micro channel;
a pair of upper and lower electrodes in the dielectric above and below said micro channel;
an impedance analyzer that applies an ac measurement signal between the electrodes to measure the impedance of the micro channel as the ratio between an ac measurement signal voltage and current;
a first conductive guard in the dielectric either between the substrate and the lower electrode or between the fluid-solid interface and the upper electrode; and
a first buffer having a first input connected to the impedance analyzer and a second input connected to a buffer output, said buffer having unity gain bandwidth larger than the ac measurement signal frequency to supply current to the first conductive guard so that its voltage closely tracks the ac measurement signal voltages applied to the lower electrode if the guard is between the substrate and the lower electrode or the ac measurement signal voltage applied to the upper electrode if the guard is between the fluid-solid interface and the upper electrode.

18. The micro sensor of claim 17, wherein a plurality of electrode pairs is spaced to measure the average impedance of a plurality of micro channels at different distances from said opening.

19. The micro sensor of claim 17, wherein the micro channel is filled with a porous dielectric material.

20. The micro sensor of claim 17, wherein said first conductive guard lies between the substrate and the lower electrode and the guard's voltage closely tracks the ac measurement signal voltage applied to the lower electrode, further comprising:
a second conductive guard in the dielectric between the fluid-solid interface and the upper electrode; and
a second buffer having a first input connected to the impedance analyzer and a second input connected to a buffer output, said buffer having unity gain bandwidth larger than the ac measurement signal frequency to supply current to the second conductive guard so that its voltage closely tracks the ac measurement signal voltages applied to the upper electrode.

21. A sensor assembly for electrochemically monitoring fluid residue, comprising:
a wafer including a micro device having a void micro feature in a dielectric layer for receiving a fluid; and
a micro sensor including
a substrate;
first, second and third fixed dielectric layers in a stack on said substrate, said third dielectric layer having a top surface that defines a fluid-solid interface for receiving the same fluid;
a buried micro channel in the second dielectric layer between the first and third dielectric layers and spaced below said fluid-solid interface, said buried micro channel configured to emulate said void micro feature;
an opening through the third dielectric layer to said buried micro channel for allowing the same fluid at said fluid-solid interface to enter the micro channel; and
at least one pair of lower and upper electrodes in the first and third dielectric layers at a fixed separation and spaced a known distance from said opening, said electrode pair configured to receive an ac measurement signal to measure the impedance of the micro channel between the electrodes as a measure of residual contamination from the fluid in the micro channel to monitor a residual contamination from the fluid of the void micro feature in the dielectric film of the micro device.

22. The micro sensor of claim 21, wherein a plurality of electrode pairs is spaced to measure the average impedance of a plurality of micro channels at different distances from said opening to monitor the residual contamination from the fluid of the void micro feature at the different distances.

23. A micro sensor for electrochemically monitoring fluid residue, comprising:
a substrate:
first, second and third dielectric layers in a stack on the substrate, said third dielectric having a top surface that defines a fluid-solid interface for receiving a fluid;
a plurality of buried micro channels in the second dielectric layer between the first and third dielectric layers and spaced below said fluid-solid interface;
at least one opening through the third dielectric layer to each said buried micro channel for allowing the fluid to enter the respective micro channel; and
a plurality of electrodes pairs in the first and third dielectric layers across said plurality of buried micro channels and spaced at different distances from their respective openings, said electrode pairs configured to receive an ac measurement signal to measure an average impedance of said plurality of buried micro channels at the different distances as a measure of residual contamination of the micro channel from the fluid at the different distances.

* * * * *